United States Patent [19]

Periasamy

[11] 4,299,770
[45] Nov. 10, 1981

[54] RECOVERY OF SUBSTITUTED PYRROLE ACETATE

[75] Inventor: Muthunadar P. Periasamy, Creve Coeur, Mo.

[73] Assignee: Mallinckrodt, Inc., St. Louis, Mo.

[21] Appl. No.: 154,377

[22] Filed: May 29, 1980

[51] Int. Cl.$^3$ ................ C07D 207/337; C07D 409/06
[52] U.S. Cl. ........................... 260/326.47; 260/326.35
[58] Field of Search ............... 260/326.47, 701, 326.35

[56] References Cited

U.S. PATENT DOCUMENTS

| | | | |
|---|---|---|---|
| 3,752,826 | 8/1973 | Carson | 260/326.47 |
| 3,846,477 | 11/1974 | Welstead, Jr. et al. | 424/272 |
| 3,952,012 | 4/1976 | Carson | 260/326.47 |
| 3,957,818 | 5/1976 | Carson | 260/326.47 |
| 3,998,844 | 12/1976 | Carson | 260/326.47 |
| 4,002,643 | 1/1977 | Carson | 260/326.47 |
| 4,048,191 | 9/1977 | Carson | 260/326.47 |
| 4,070,368 | 1/1978 | Carson | 260/326.47 |
| 4,119,639 | 10/1978 | Carson | 260/326.47 |
| 4,187,230 | 2/1980 | Wegand et al. | 260/326.47 |
| 4,213,905 | 7/1980 | Carson | 260/326.47 |

FOREIGN PATENT DOCUMENTS

876488 9/1961 United Kingdom .

OTHER PUBLICATIONS

Carson et al.; J. Med. Chem. vol. 16, pp. 172-174, (1973).

Primary Examiner—Alton D. Rollins
Attorney, Agent, or Firm—Bernard, Rothwell & Brown

[57] ABSTRACT

A process is provided for the recovery of aroyl-1,4-di (lower alkyl)-pyrrole-2-acetate in its lower alkyl ester form from an aqueous liquid medium initially containing said acetate in either its salt or lower alkyl ester form. The acetate ester in the aqueous medium can be saponified to salt form and a crop thereof can be recovered by cooling the medium to form a salt product which is insoluble in the remaining aqueous mother liquor. Subsequently, another crop of crude pyrrole salt can also be recovered from the mother liquor by concentrating the mother liquor. The resulting additional pyrrole acetate salt can be converted back into the acetate lower alkyl ester, which ester can then be recycled to a next batch of aqueous medium containing aroyl-1,4-di (lower alkyl)-pyrrole-2-acetate salt and/or ester.

10 Claims, No Drawings

RECOVERY OF SUBSTITUTED PYRROLE ACETATE

The present invention relates to an improved method for recovering and purifying substituted pyrrole acetate materials at the completion of the synthesis procedure used to produce them. Sodium 5-(p-chlorobenzoyl)-1,4-dimethylpyrrole-2-acetate, known by the trade name Zomepirac, is an analgesic and anti-inflammatory drug. Zomepirac, and other pharmaceutically similar materials, as well as methods for their preparation, are disclosed, for example, in J. R. Carson and Stuart Wong, *Journal of Medicinal Chemistry*, 1973; Vol. 16, No. 2 Page 172 and in the following U.S. Patents issued to J. R. Carson: U.S. Pat. Nos. 4,070,368; 4,048,191; 4,002,643; 3,998,844; 3,957,818; 3,865,840; 3,846,477 and 3,752,826.

In one synthesis method as set forth in such references, the final steps for production of a desired substituted pyrrole acetate product involve the aroylation at the 5-position of a substituted pyrrole acetate ester of the formula:

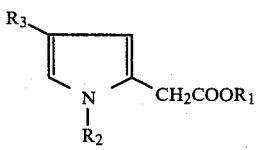

wherein $R_1$, $R_2$, and $R_3$ are lower alkyl. Aroylation can be carried out using an aroyl halide aroylating agent, e.g., of the formula:

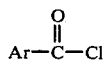

wherein Ar is an aryl group as hereinafter more fully defined. Aroylation is generally conducted in a conventional manner using conventional aroylation conditions including utilization of a Lewis acid catalyst and a solvent suitable for carrying out a Friedel Crafts-type reaction.

After aroylation is completed to the extent desired, the resulting 5-aroylated substituted pyrrole acetate ester is recovered from the aroylation reaction medium. This acetate ester is generally thereafter saponified in an aqueous liquid medium to provide the desired substituted pyrrole acetate in salt form. This product salt can be recovered from the aqueous saponification medium by cooling the medium and separating the resulting insoluble, substituted pyrrole acetate salt from the aqueous mother liquor in which it has formed. It is, of course, apparent that improved recovery of the pyrrole acetate salt from the aqueous mother liquor after saponification will increase the overall yield of the desired pharmaceutical product. Accordingly, it is an object of the present invention to provide an improved method for the recovery and purification of pyrrole acetate from the aqueous liquid medium which contains the salt form of said pyrrole acetate.

In accordance with the present invention, this objective can be realized by separating a crop of substituted pyrrole acetate salt precipitated from the aqueous saponification reaction medium, thereafter concentrating the remaining mother liquor to form another crop of solid, crude pyrrole acetate salt which can also be recovered, subsequently converting the latter crop of crude pyrrole acetate salt back into the acetate ester and recycling the resulting ester product to the next batch of substituted pyrrole acetate-containing aqueous liquid medium for saponification.

The aroyl-substituted, 1,4-di(lower alkyl)-pyrrole-2-acetate materials of the present invention have the following general structural formula:

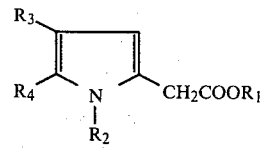

wherein $R_1$ is a salt-forming cation or is an ester-forming lower alkyl group; $R_2$ and $R_3$ are lower alkyl groups; and $R_4$ is

wherein Ar represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano and methylthio.

As used herein, the terms "lower alkyl" and "lower alkoxy" include such groups that are straight or branched chain saturated hydrocarbons having from 1 to about 6 carbon atoms such as, for example, methyl, ethyl, propyl, isopropyl, butyl, pentyl, hexyl and the like alkyls, and, respectively, the corresponding alkoxy groups such as methoxy, ethoxy, propoxy, isopropoxy, etc.

Preferred $R_1$ salt-forming cations include alkali metal cations such as sodium and potassium. The preferred $R_1$ ester-forming lower alkyl groups are methyl and ethyl. The preferred $R_2$ and $R_3$ substituents are methyl. The preferred $R_4$ group is p-chlorobenzoyl. The preferred acetate salt for use in the present recovery process is sodium 5-(p-chlorobenzoyl)-1,4-dimethylpyrrole-2-acetate, known by the trade name Zomepirac.

In the recovery process herein, the aroyl-substituted, 1,4-di(lower alkyl)-pyrrole-2-acetate, in its lower alkyl ester form, can be saponified under saponification conditions in an aqueous liquid reaction medium. Saponification can be carried out using conventional saponification agents such as, for example, sodium hydroxide, potassium hydroxide, ammonium hydroxide, and the like. Saponification conditions can include reaction medium temperatures in the range of from about 20° C. to 100° C., preferably from about 50° C. to 90° C. The time of the saponification reaction can vary from about 1 to 10 hours, preferably from about 2 to 4 hours.

At the completion of the saponification reaction, the aqueous salt solution is cooled under conditions sufficient to form within the aqueous medium a crop of insoluble pyrrole acetate salt. Cooling conditions can, for example, include maintenance of aqueous medium temperatures of from about −15° C. to 25° C., preferably about −5° C. to 5° C., for a period of from about 1 to 2 hours. The insoluble crop of pyrrole acetate salt is thereafter precipitated and separated from the cooled aqueous mother liquor as product. Separation can be effected by conventional liquid-solid separation techniques such as, for example, by centrifugation, filtration, and the like.

After separation of a crop of desired pyrrole acetate salt product, remaining aqueous mother liquor is further treated in accordance with the present invention in order to recover therefrom additional material from which desired pyrrole acetate product can eventually be realized. Thus, after separation of a crop of pyrrole acetate salt, the remaining aqueous mother liquor can be concentrated in order to bring about formation in the concentrated mother liquor of another crop of crude insoluble pyrrole acetate salt material. Concentration can be carried out by removing from the mother liquor about 75% to about 95%, preferably about 85% to 90%, by weight of the mother liquor, of water after the insoluble previous crop of product has been recovered therefrom. Concentration generally can be effected by heating the mother liquor to evaporate water vapor therefrom to the desired extent. Upon concentration of the mother liquor, another insoluble crop of crude pyrrole acetate salt is formed in the concentrated mother liquor. This crop of pyrrole acetate salt preferably can then be separated from the concentrated mother liquor in a similar or other manner as the previous crop was recovered. It is, however, not necessary to separate this crop of pyrrole acetate salt before subsequent processing steps are carried out.

The crop of pyrrole acetate salt formed after concentration of the mother liquor contains a number of impurities. Because of the nature and amount of these impurities, it is not possible to purify such crop of pyrrole acetate salt by a simple recrystallization procedure. Nor is it advisable to recycle this crop of salt by simply mixing it with the next batch of pyrrole acetate salt solution before such solution is cooled to precipitate a crop of the salt. Instead, in accordance with the present invention, the crop of crude pyrrole acetate salt formed after the described mother liquor is concentrated is converted back into the pyrrole acetate ester, which ester product is then recycled to an aqueous liquid medium containing aroyl 1,4-di(lower alkyl)-pyrrole-2-acetate ester from the normal synthesis process, e.g., aqueous liquid medium containing product formed by the thermal benzoylation of pyrrole ester.

Conversion into the corresponding ester of the crude crop of pyrrole acetate salt formed in and preferably recovered from the concentrated mother liquor may be accomplished under conventional alkylating conditions. Typically, this crude crop material can be reacted with an alkylating agent in a reaction medium, which is preferably an essentially anhydrous reaction medium, under conditions which will form the desired ester product. Alkylating agents can include, for example, di-(lower alkyl) sulfates such as dimethyl sulfate and diethyl sulfate, and lower alkylhalides such as methyl iodide, ethyl iodide, methyl bromide, ethyl bromide, methyl chloride, ethyl chloride and the like. Alkylating agents can be employed, for example, in a molar ratio of alkylating agent to pyrrole acetate salt of from about 1:1 to 5:1.

The crude pyrrole acetate salt is preferably dried before it is introduced into the reaction medium for conversion to the corresponding pyrrole acetate ester material. Generally, the crude salt product which can be separated from the concentrated saponification aqueous mother liquor may be dried to the dihydrate stage before being added to the reaction medium for conversion to the acetate ester product.

The reaction medium for conversion of the salt to ester can be provided, for example, by alkylating the crude salt product in a solvent, e.g., an alkanol solvent such as, for example, methanol or ethanol, or a lower alkyl ketone such as acetone. Mixtures of such solvents, e.g. methenol and acetone, may also be employed.

Such a reaction solvent can be employed in amounts sufficient to dissolve the reactants. Typically, weight ratios of solvent-to-reactants of from about 3:1 to 6:1 can be utilized.

Reaction conditions suitable for converting the second crop pyrrole acetate salt material to the pyrrole acetate ester can include reaction medium temperatures in the range of from about 25° C. to 125° C., preferably about 55° C. to 90° C., using reaction times of from about 1 hour to 10 hours, preferably about 3 to 6 hours. Typically, heating of the reaction medium under reflux conditions can be carried out.

Conversion of the salt to ester is generally continued until pyrrole acetate salt material substantially disappears. This reaction involving conversion of the pyrrole acetate salt to the corresponding lower alkyl ester can then be quenched by adding water to the reaction medium. Cooling of the quenched reaction medium, typically to a temperature of from about 0° C. to 10° C., will result in the formation of insoluble ester product which can then be separated from the reaction medium by conventional means as hereinbefore described. After separation from the quenched reaction medium, the ester product generally can be rinsed with the reaction medium liquid, washed, and then recycled to the aqueous liquid medium as hereinbefore described.

Remaining quenched reaction medium material from the ester conversion reaction is generally treated with caustic and refluxed for a period of time before it is discarded. Treatment of this nature serves to destroy the toxic alkylating agent remaining in the quenched reaction medium solution.

the improved recovery and purification process of the present invention is illustrated by the following example:

EXAMPLE I

About 31 grams of the lower alkyl ester form of 5-(p-chlorobenzoyl)-1,4-dimethylpyrrole-2-acetate are saponified in 225 ml. of an aqueous reaction medium containing 0.12 M.NaOH. Saponification is carried out at about 90° C. for a period of from about 2 to 4 hours. At the end of this period, the aqueous saponification medium is cooled to a temperature of 0° to 5° C. The resulting insoluble first crop of acetate salt product is removed from the aqueous mother liquor. An 86–88% yield of Zomepirac [sodium 5-(p-chlorobenzoyl)-1,4-dimethylpyrrole-2-acetate] is thereby realized based on the amount of ester initially employed.

After removal of the first crop of Zomepirac, the remaining aqueous mother liquor is concentrated by removing about 85% by weight of the mother liquor of water therefrom. Upon concentration, an additional amount of second crop Zomepirac product is formed in the concentrated aqueous mother liquor and is removed therefrom by filtration. A yield of 3–6% (based on the initial feed ester) of this second crop of crude Zomepirac is thus obtained.

About 300 ml of anhydrous methyl alcohol, 52.5 g of the second crop Zomepirac, dried to at least its dihydrate stage (maximum L.O.D.≃11.2), and 19 ml of dimethyl sulfate (a carcinogen requiring extreme care in its handling) are then charged to a 500 ml three-necked flask fitted with a mechanical stirrer, condenser and thermometer. The mixture is refluxed at 67°–68° C. for 3 to 6 hours.

Ater the first ½ to 1 hour of reflux, formation of solid materials is observed. At the end of 3 hours, the reaction is checked for completion. About 75 ml of water are added to the reaction mixture, and the reflux is continued for 30 minutes at 74°–75° C. The solution is then cooled to 2°–3° C. for one hour, using an ice-salt mixture.

The reaction mixture is thereafter filtered to recover a solid product. The resulting solid is rinsed with the reaction medium solution and is then washed with 60 ml of an ice cold mixture of 4 parts methanol to 1 part water. The wash is combined with the remaining reaction medium (≃425 ml.) and saved for subsequent treatment. The product is dried in an oven at 80° C. for 6–8 hours. The resulting yield is 32–42 g (70–90%) which varies according to the amount of impurities present in the second crop Zomepirac starting material.

The combined reaction medium/wash is treated for elimination of unreacted dimethyl sulfate by adding 8 g (0.2 mol) of NaOH to the solution and refluxing for 2 hours. After cooling, the resulting solution is discarded.

What is claimed is:

1. A process for the recovery and purification of an aroyl-1,4-di(lower alkyl)-pyrrole-2-acetate product from an aqueous medium containing said pyrrole acetate, in either its salt or lower alkyl ester form, said process comprising:
    (A) saponifying that aroyl-1, 4-di(lower alkyl)-pyrrole-2-acetate which is present in its lower alkyl ester form under saponifying conditions to thereby convert said ester to salt form in the aqueous medium;
    (B) cooling said aqueous medium to a temperature and for a time period sufficient to precipitate a crop of said aroyl-1,4-di(lower alkyl)-pyrrole-2-acetate salt, which crop is insoluble in the remaining aqueous mother liquor;
    (C) separating as product said insoluble acetate salt from said aqueous mother liquor;
    (D) thereafter concentrating said aqueous mother liquor to the extent sufficient to precipitate another crop of crude aroyl-1,4-di(lower alkyl)-pyrrole-2-acetate salt, which crop is insoluble in said concentrated mother liquor;
    (E) converting said crop of crude aroyl-1-4-di(lower alkyl)-pyrrole-2-aceta e salt under conversion reaction conditions into the lower alkyl ester form of said aroyl-1,4-di(lower alkyl)-pyrrole-2-acetate; and
    (F) recovering said esterified crop of aroyl-1,4-di(lower alkyl)-pyrrole-2-acetate and thereafter recycling said recovered acetate ester material to an aqueous medium for saponification in accordance with Step A.

2. A process according to claim 1 wherein the di(lower alkyl)-pyrrole substituents are both methyl, the aroyl pyrrole substituent is p-chlorobenzoyl and the lower alkyl ester group is selected from methyl and ethyl.

3. A process according to claim 1 or 2 wherein the saponifying agent utilized is sodium hydroxide and saponification is carried out at a reaction medium temperature of from about 20° C. to 100° C.

4. A process according to claim 1 or 2 wherein after saponification the aqueous reaction medium is cooled to a temperature of from about −15° C. to 25° C. to form the crop of substituted pyrrole acetate salt.

5. A process according to claim 1 or 2 wherein, after removal of acetate salt in step (C), the remaining aqueous mother liquor is concentrated to remove from about 75% to 95% by weight of aqueous mother liquor, of water therefrom, to thereby form said crop of insoluble crude acetate salt.

6. A process according to claim 1 or 2 wherein said crop of crude substituted pyrrole acetate salt is coverted to the corresponding lower alkyl ester material in a reaction medium comprising a solvent selected from methanol and ethanol, using an alkylating agent selected from di(lower alkyl) sulfates and lower alkyl halides.

7. A process according to claim 6 wherein conversion of the salt to ester occurs by using a molar ratio of alkylating agent to acetate of from about 1:1 to 5:1, in a reaction medium having a weight ratio of solvent to reactants of from about 3:1 to 6:1.

8. A process according to claim 7 wherein conversion of the salt to ester is conducted in a reaction medium maintained at a temperature of from about 25° C. to 125° C.

9. A process according to claim 8 wherein after the conversion of salt to ester, the esterified product is recovered from the reaction medium by cooling the reaction medium to a temperature of from about 0° C. to 10° C.

10. A process for the recovery and purification of 5-(p-chlorobenzoyl)-1,4-dimethyl-pyrrole-2-acetate from an aqueous liquid medium containing said acetate, said process comprising:
    (A) saponifying the ester form of said acetate using sodium hydroxide in an aqueous reaction medium maintained at a temperature of from about 50° C. to 90° C. to convert said acetate to its sodium salt form in the aqueous saponification reaction medium;
    (B) cooling said aqueous reaction medium to a temperature of from about −5° C. to 5° C. to precipitate a first crop of sodium 5-(p-chlorobenzoyl)-1,4-dimethylpyrrole-2-acetate;
    (C) separating as product said precipitated acetate salt from the remaining aqueous mother liquor;
    (D) thereafter concentrating said mother liquor remaining after first crop separation by removing from said mother liquor from about 85% to 90% of its weight of water to thereby precipitate a second crop of crude sodium 5-(p-chlorobenzoyl)-1,4-dimethylpyrrole-2-acetate;
    (E) separating said second crop of crude acetate salt material from said concentrated aqueous mother liquor;
    (F) converting said separated second crop of crude acetate salt material to the corresponding methyl of ethyl ester form of said acetate by reacting said salt with an alkylating agent selected from dimethyl sulfate, diethyl sulfate, methyl iodide, ethyl iodide, methyl bromide, ethyl bromide, methyl chloride and ethyl chloride, in a reaction medium containing a solvent selected from methanol, ethanol, and acetone, wherein the molar ratio of alkylating agent to pyrrole acetate ranges from about 1:1 to 5:1 and reaction medium is maintained at a temperature of from about 55° C. to 90° C. to effect conversion to the ester product;

(G) recovering the esterified second crop product from the reaction medium by cooling the reaction medium to a temperature of from about 0° C. to 10° C., to precipitate an insoluble product which is removed from said reaction medium; and (H) recycling said recovered second crop acetate product to aqueous liquid medium for saponification in accordance with step A.

* * * * *